United States Patent [19]

Lary et al.

[11] Patent Number: 4,845,025
[45] Date of Patent: Jul. 4, 1989

[54] BIOLOGICAL SAMPLE MIXING APPARATUS AND METHOD

[75] Inventors: Todd P. Lary; Jorge A. Quintana; Osvaldo E. Miranda, all of Miami; John R. DeChristopher, Sr., Davie; John D. Hollinger, Miami, all of Fla.

[73] Assignee: Coulter Corporation, Hialeah, Fla.

[21] Appl. No.: 119,018

[22] Filed: Nov. 10, 1987

[51] Int. Cl.[4] .......................... A01N 1/02; C12M 1/02; G01N 33/48

[52] U.S. Cl. ........................................ 435/2; 435/316; 366/111; 366/211; 422/99; 422/100

[58] Field of Search .................... 435/2, 286, 315, 316, 435/312; 422/99, 100; 366/110, 111, 208, 210, 211; 74/86

[56] References Cited

U.S. PATENT DOCUMENTS

| | | | |
|---|---|---|---|
| 547,596 | 10/1895 | Brantingham | 74/86 X |
| 982,156 | 1/1911 | Miltz | 366/216 |
| 1,852,376 | 4/1932 | Rees | 177/118 |
| 2,480,502 | 8/1949 | Nieder | 134/118 |
| 2,779,510 | 1/1957 | Wilson et al. | 222/193 |
| 2,828,949 | 4/1958 | Paladino et al. | 366/111 |
| 2,846,201 | 8/1958 | Mermelstein | 366/111 |
| 3,061,280 | 10/1962 | Kraft et al. | 366/110 |
| 3,353,796 | 11/1967 | Roberts | 366/111 X |
| 3,975,001 | 8/1976 | Moore et al. | 366/111 |
| 4,162,129 | 7/1979 | Bartholomew, Jr. | 366/211 |
| 4,305,668 | 12/1981 | Bilbrey | 366/11 |
| 4,529,705 | 7/1985 | Larsen | 436/17 |
| 4,751,052 | 6/1988 | Schwartz et al. | 422/100 |

FOREIGN PATENT DOCUMENTS 143357  10/1953  Sweden ............................ 366/111

*Primary Examiner*—Albert J. Makay
*Assistant Examiner*—Allen J. Flanigan
*Attorney, Agent, or Firm*—Carl Fissell, Jr.; Gerald R. Hibnick

[57] ABSTRACT

Automatic biological sample mixing apparatus for use in flow cytometry, wherein a sample container is secured loosely at its top by means of a multi-reagent dispensing head; and the container is mounted at its bottom on a resilient support disposed on an elliptically rotated member, to cause reagents introduced into the container to be thoroughly mixed with a sample in the container in a fast, efficient, gentle, and accurately repeatable manner.

24 Claims, 5 Drawing Sheets

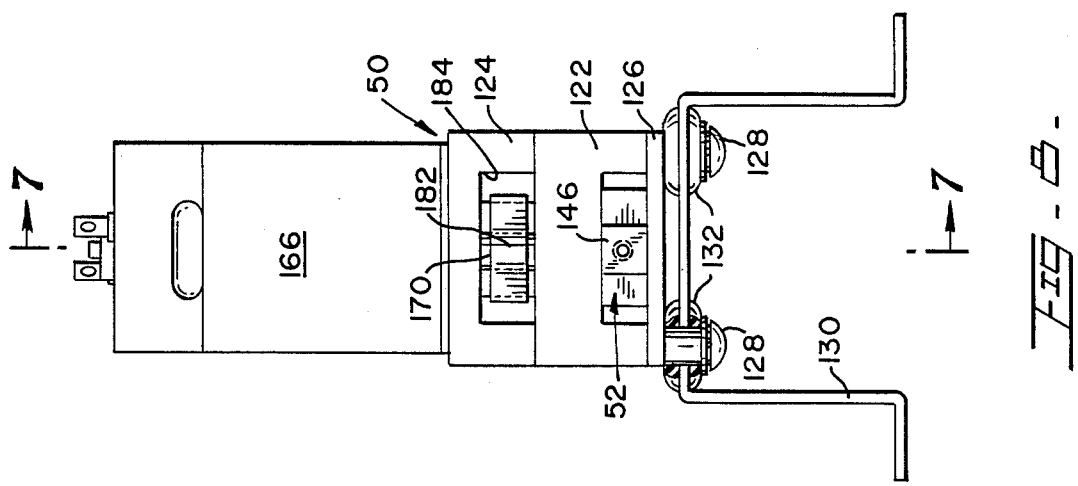
FIG-6-
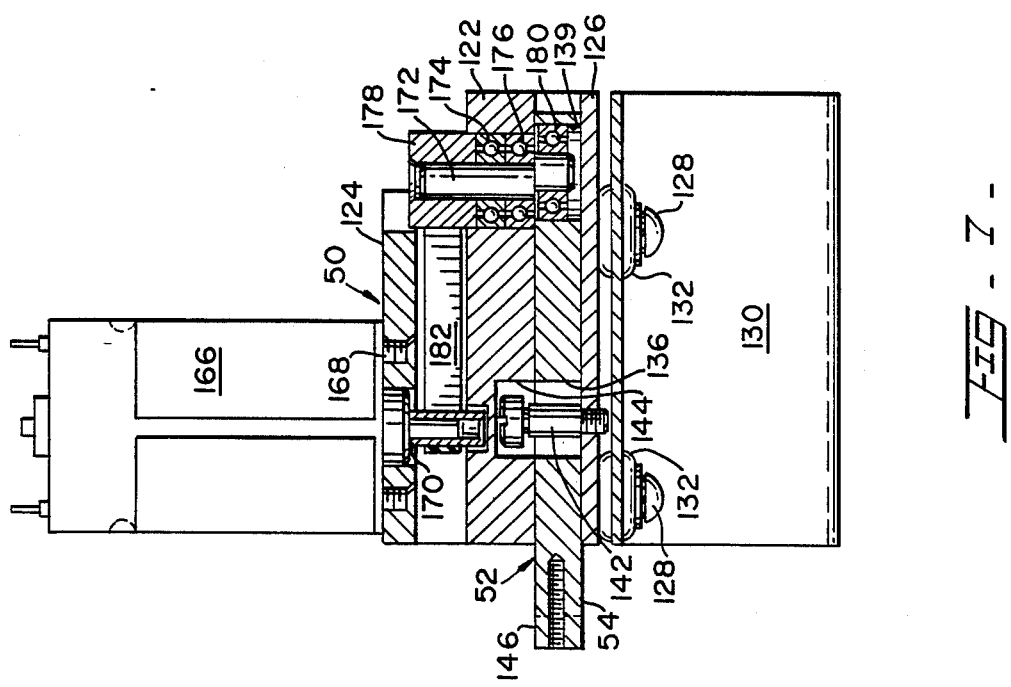
FIG-7-
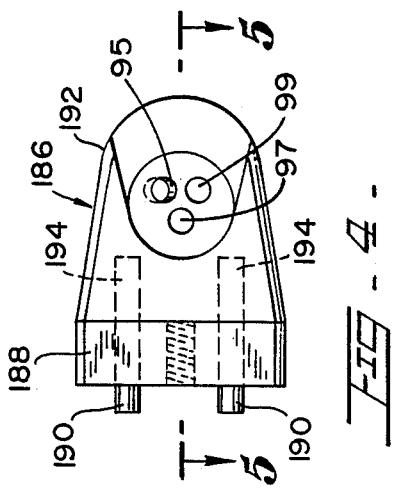
FIG-4-
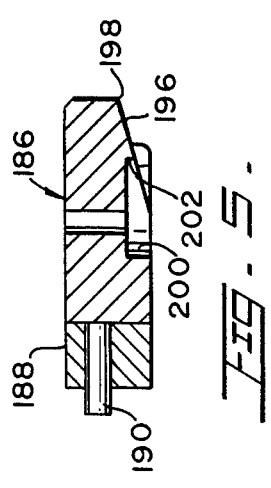
FIG-5-
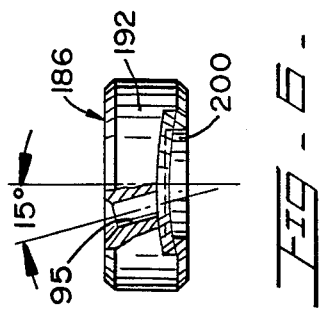
FIG-6-

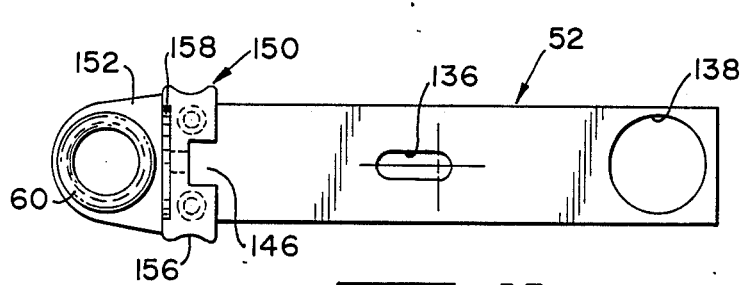
FIG_14.
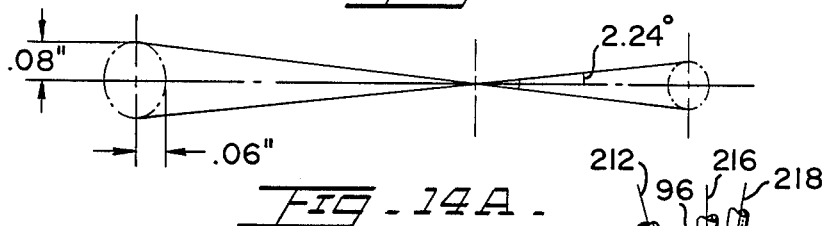
FIG_14A.
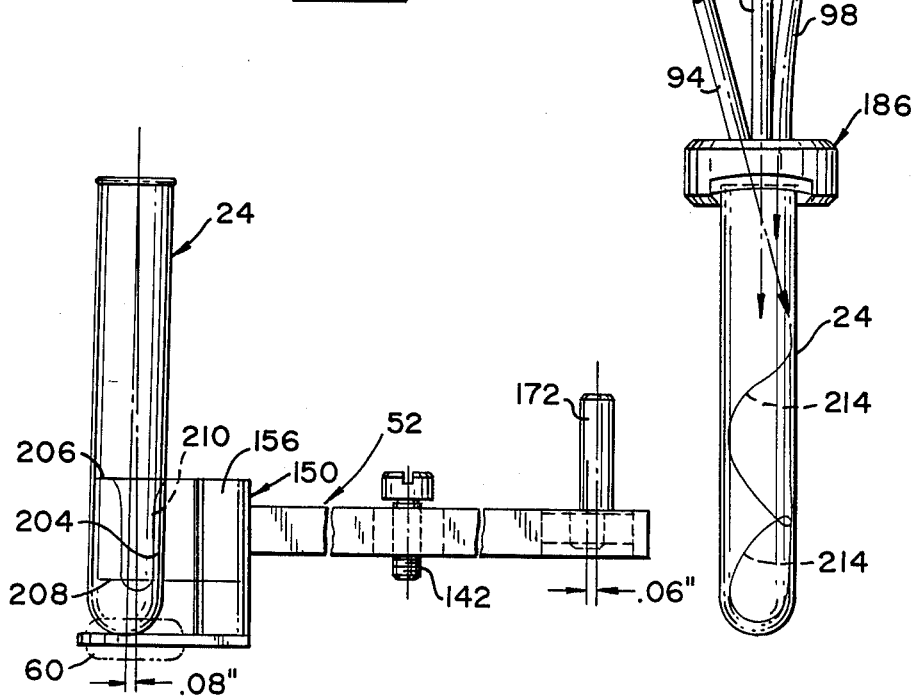
FIG_15.
FIG_16.

BIOLOGICAL SAMPLE MIXING APPARATUS AND METHOD

BACKGROUND OF THE INVENTION

1. FIELD OF THE INVENTION

The present invention relates to apparatus for biological sample preparation and, more particularly, to apparatus for automatically mixing hematological sample material with chemical reagents in a rapid, gentle, specific, selectable, controllable timed sequence.

2. DESCRIPTION OF THE PRIOR ART

Flow cytometry provides investigators with data on physical parameters of particles, for example, human cells. One of the cell types of greatest interest is the human leukocyte (white cell). Human leukocytes can be classified into different classes and subclasses. These classifications in part are made by comparing data from physical measurements made on these cells. These measurements include cell volume and granularity. Immunological classification can be performed by using monoclonal antibodies tagged with fluorescent compounds. Physical measurements can be used to classify white cells into three major groups, for example, lymphocytes, monocytes, and granulocytes. Immunofluorescent measurements can be used to classify the lymphocytes into subclasses, for example, T-cells, B-cells, etc. Immunofluorescence also can be used to further classify the T-cells into at least two categories, for example, cytotoxic cells, and suppressor cells, etc. The ability to classify human white cells has provided investigators with valuable diagnostic information. However, in order for investigators to analyze leukocytes with flow cytometry, the sample must be free of other cell types, such as red blood cells. Therefore, sample preparation is an important step required to insure rapid reproducible results.

The current methods of leukocyte preparation for immunofluorescence include whole blood lysis techniques and density gradient separation techniques. The major lytic techniques use either ammonium chloride or detergents to lyse red cells. These lytic techniques require the immunological staining to take place before red cell lysis. The current techniques fix or require fixation of the leukocytes immediately after lysis, in order to maintain sample stability. In current commercially available lytic procedures, the sample must be washed at least once sometime during the procedure. Lytic techniques have the advantage of requiring only 100 μl of whole blood per sample to perform each test. In density gradient separation, the lymphocytes are separated from most of the other blood cells on the basis of their buoyant density. This technique usually requires between 3 and 6 ml of whole blood in order to perform several stainings. It also differs from lytic techniques because the immunofluorescent staining is carried out after the lymphocytes are removed from the red blood cells. Density gradient separation also requires that the sample be washed at least one during the procedure. One advantage of density gradient separations is that they do not require immediate fixation after the lymphocytes are stained.

All the above mentioned preparation techniques are manual in nature. In lytic techniques, the operator monitors the lyse times and the sample must be visually monitored for complete red cell lysis. In density gradient methods, the operator must remove the specific density layer containing the lymphocytes without collecting any other cells in other layers. In addition, the operator must centrifuge then wash away unwanted material. Obviously, this activity risks biohazard contamination and cell viability. These manual techniques contribute to variability in flow cytometric data.

SUMMARY OF THE INVENTION

One intended use of the present automatic, rapid sample preparation system, but not limited thereto, is to prepare leukocytes for immunofluorescent measurements on optical flow cytometers. The apparatus comprises a single unit containing a mixing device, a syringe chemical reagent delivery system, and timing electronics. The chemical reagent delivery system includes three liquid chemical reagents. These three reagents are: red cell lytic reagent of the formulation 1.2 mL formic acid, 0.2 mL sodium omadine (40%), and 998.6 mL deionized water; lysis stabilizing reagent of the formulation 31.30 grams sodium sulfate, 14.05 grams sodium chloride, 6 grams sodium carbonate, and 1 liter deionized water; and a fixative reagent of the formulation 6.05 grams TRIS (HCL) buffer, 10 grams paraformaldehyde, and 0.05 mL sodium hydroxide (50%). The actual red cell lysis time is about eight seconds with the new lytic reagent, compared with at least two minutes with current commercially available flow cytometric lysis techniques. The present sample preparation system can operate in either of two modes. A short cycle mode is provided, which uses whole blood which has been immunofluorescently stained before the sample is introduced into the unit for red cell lysis; and a long cycle is provided, in which a sample is first immunofluorescently stained on the unit and then red cell lysis is performed.

The present system hardware and method are designed to provide ease of use and simple operator maintenance. The reagent delivery section is composed of three motor driven displacement syringes. Each of these syringes can be primed easily or replaced by the operator. The timing electronics provides both cycled syringe delivery or individual syringe priming. A system reset mechanism also is provided for immediate cycle termination. The system mixing apparatus comprises a rotating arm which contains a rubber grommet to support a test tube. The top of the test tube is held in a defined position, and the tube rotates at its bottom. This type of mixing allows the contents of the tube to be mixed gently in the unique fashion described herein. The mixer rotates the tube at approximately 1,500 rpm.

This system has several advantages. First, the system does not require any sample washing procedures. Thus, the sample will have no cell loss due to washing. Second, the rapid, gentle nature of the system does not require sample fixation for sample stability. The sample fixative is provided in order to preserve samples for long periods of time and provide effective biohazard sterilization. Third, the present sample preparation system is designed to prepare samples in 12×75 mm test tubes. This type of test tube is used with most flow cytometers. Therefore, the technician can run his sample analysis in the same tube used to prepare the sample. Other systems use separate tubes for separate steps. Fourth, by analyzing unwashed samples, it has been found that the number of B-cell lymphocytes is closer to the normally reported clinical values than found using the current sample preparation techniques. However, the greatest advantage of the system is that it provides a rapid, automated, standardized sample preparation technique for the flow cytometer equipped lab. Variability of result is held to a bare minimum. This type of system greatly reduces the operator's manual labor during the sample preparation. In addition, the system is designed to use commercially, and generally readily available, monoclonal antibodies and staining procedures.

BRIEF DESCRIPTION OF THE DRAWINGS

FIG. 4 is a bottom view of the dispensing member of FIG. 2, showing it two part attachment;

FIG. 5 is a sectional side view of the front portion of the dispensing member of FIG. 4;

FIG. 6 is a detail view of the canted or angled inlet portion of the dispensing member of FIGS. 2-5;

FIG. 7 is a sectional, side-elevational view of the mixing apparatus of the present invention;

FIG. 8 is a front view of the mixing unit of the present apparatus taken along line 7—7;

FIG. 14 is a top plan view of a modified mixing arm for the present invention;

FIG. 14A is a diagrammatic illustration of the motion patterns of the front vs. the rear of the mixing arm.

FIG. 15 is a view illustrating the vortex created by the present mixing apparatus; and FIG. 16 is a front view of the container of this invention illustrating the reagent fluid entering angles.

BRIEF DESCRIPTION OF THE PREFERRED EMBODIMENT OF THE INVENTION

The apparatus incorporating the present invention can be characterized as a sample preparation device, which can be used by a laboratory technician to automatically, reproducibly, quickly, and simply lyse, stabilize, and fix hematologic (human blood) samples for further investigation. The apparatus comprises: a central mixing mechanism; a reagent delivery system of fluid dispensing syringes or pumps; and control circuitry and mechanisms for stopping, starting, timing, and proportioning the chemical reagents employed with the apparatus.

Figure 1:
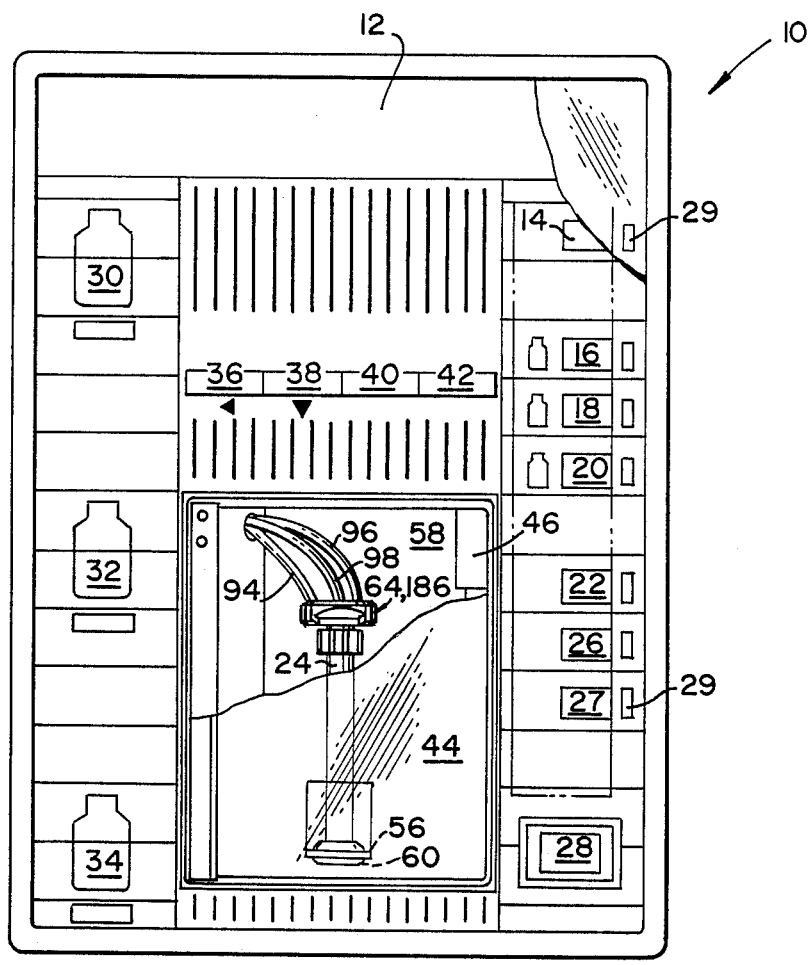
FIG. 1 is a front view of apparatus incorporating the present invention and illustrates the control switches and reagent container viewing windows.

FIG. 1 illustrates the apparatus 10 embodying the present invention. The base apparatus 10 is a stand-alone, self-contained, operational, unitary assembly including various controls providing different required functions for enabling the apparatus 10 to perform the hereinafter described sample preparation. As seen in FIG. 1, the base apparatus 10 comprises a rectangular, box-like container including a front panel 12 provided with a plurality of hereinafter enumerated and listed membrane switches for specified functions. A stop switch 14 aborts any function of the apparatus. A syringe A switch 16 dispenses reagent A from a reagent bottle A. A syringe B switch 18 dispenses reagent B from a reagent bottle B, and a syringe C switch 20 dispenses reagent C from a reagent bottle C. A mix switch 22 stirs the contents of a mixing container, for example, a test tube 24, in a manner described later herein. Two switches 26 and 27 are employed to initiate a 35 second preparation operating cycle or a 93 second preparation operating cycle, respectively. A power switch 28 is a rocker type on-off switch. Each of the listed membrane switches is provided with an indicator light 29 for indicating to the operator the present status of the particular function. Reagent bottle viewing windows 30, 32, and 34 enable the operator to check the fluid level in each reagent bottle A, B, or C through the respective window.

Message indicators 36, 38, 40, and 42, for example, LED's, light to indicate to the operator that certain action needs to be taken with respect to: close the side door 76, close the front door 44, sample preparation aborted, or that the apparatus is ready for operation. Each of these functions will become clear as the description proceeds. The reagent bottle A contains a lytic reagent. The reagent bottle B contains a stabilizer, and the reagent bottle C contains a fixative.

A front door interlock 46, disposed at the upper right hand corner of the transparent door 44, is connected into the electronic control circuitry (not shown). A side door interlock 48 (FIG. 9) likewise is connected to the electronic control circuitry. Both interlocks 46 and 48 are wired into the electronic control circuitry as sensing devices to signal the microprocessor of the control circuitry that a door is open so as to avoid biohazard contamination and possible operator injury.

Figure 12:
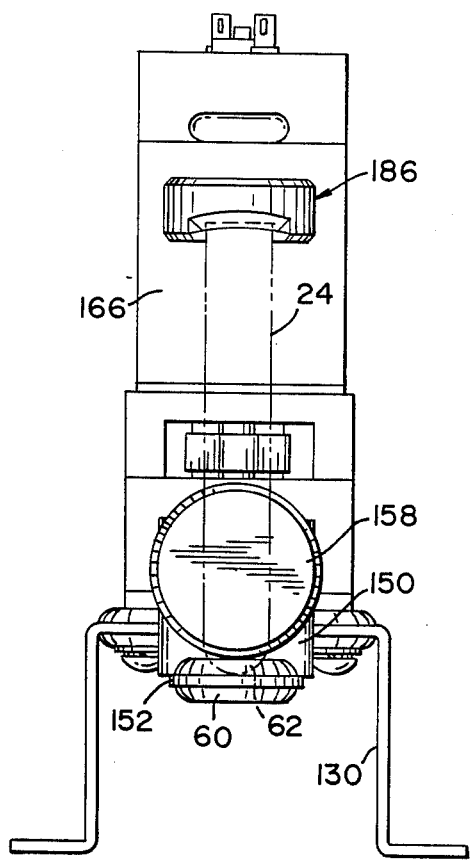
FIG. 12 is a front view of a modified sample container attachment apparatus.

FIGS. 7 and 8 illustrate the mixing mechanism 50, which is seen to comprise an elongated mixing arm 52, the forward end portion 54 of which extends forwardly through a slot or opening 56 (FIG. 1) in the front wall 58 of the apparatus 10. The arm 52 has disposed thereon a resilient member 60, for example, a rubber grommet, shaped so as to receive and support the rounded bottom end 62 (FIG. 12) of a conventional test tube 24, earlier briefly described.

Figure 11:
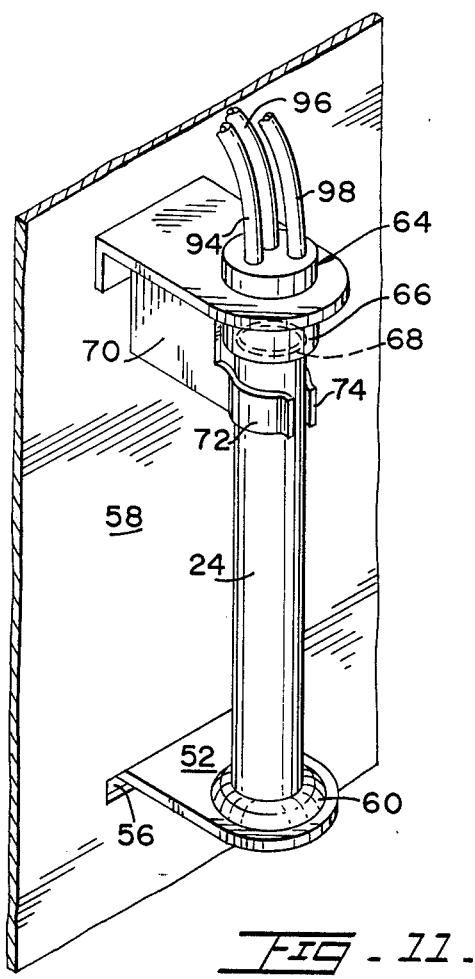
FIG. 11 is an isometric view of one form of sample container attachment apparatus.

A fluid dispensing member 64 (FIGS. 2-6 and 11) provides a pseudo-enclosure 66 for the open top end 68 (FIG. 11) of the mixing container shown as test tube 24 and is disposed above the mixing arm 52 (FIGS. 7 and 8) a sufficient distance to accommodate the test tube 24. Immediately below the fluid dispensing member 64 is a flexible, open, U-shaped clip 70 (FIG. 11). Two opposing arms 72 and 74 of the clip 70 extend from the lower portion of the fluid dispensing member 64 for receiving and partially surrounding and holding the upper open end 68 of the test tube 24.

Figure 9:
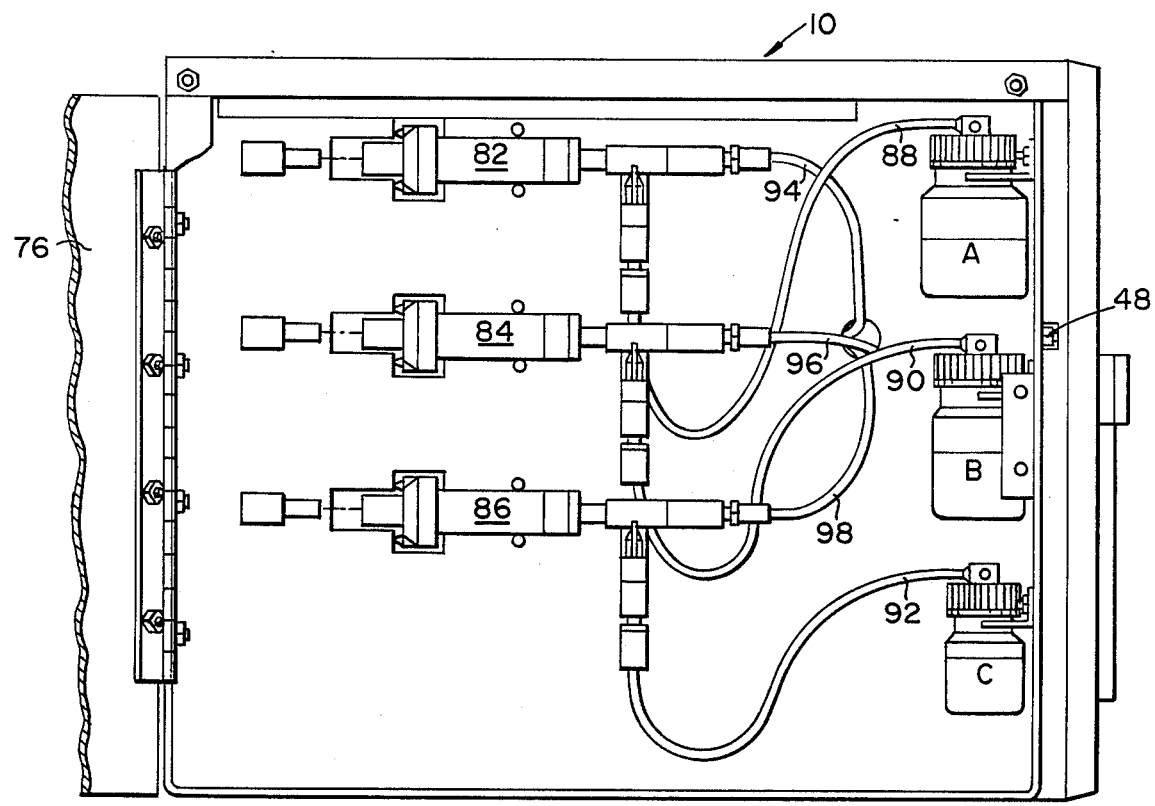
FIG. 9 is a left side view of the apparatus of FIG. 1 illustrating the reagent syringe pumps.
Figure 10:
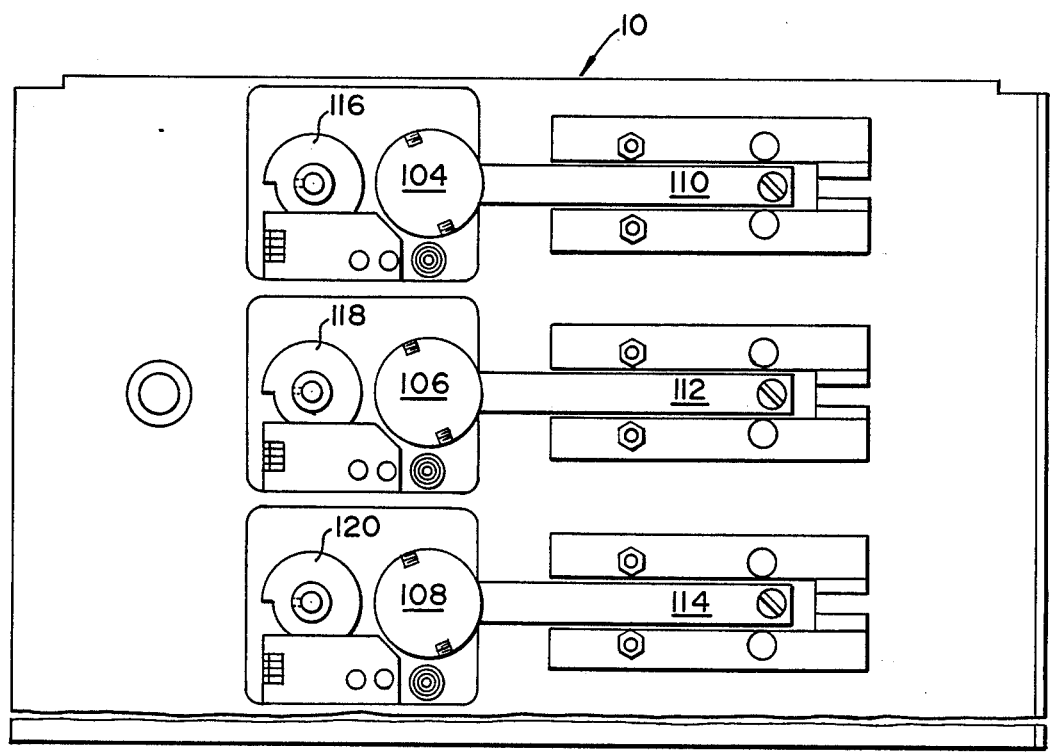
FIG. 10 is a right side view of the syringe pump actuating mechanism.

As seen in FIG. 9, the left side of the apparatus 10 is provided with a hinged cover member or door 76 of solid material such as sheet metal. The right hand portion of the door 76 includes a member (not shown) cooperating with the door interlock member 48 to indicate that the door is closed for activating the door LED 36 message indicator (FIG. 1). Arranged in parallel along the left side of a rigid, separating wall member 80 of the apparatus 10, are disposed three liquid, syringe type dispensers or pumps 82, 84, and 86. Input tubes 88, 90, and 92 of flexible, chemically inert material connect the respective containers A, B, and C of reagent fluid to the liquid dispensers 82, 84, and 86. Output tubes 94, 96, and 98 from the liquid dispensers 82, 84, and 86 are secured to the top of the fluid dispensing member 64, as seen, for example, in FIGS. 1, 2, 3, 4 and 11 of the drawings. Each of the fluid output tubes 94, 96, and 98 is connected to a respective port 95, 97 and 99 of the fluid dispensing member 64. Each port 95, 97 and 99 is provided with a short inserted length of constricting tubing 100 in order to accelerate the fluid flow in these fluid dispensing members, to aid in fluid break-off, as will become more apparent later on herein. The liquid dispensers 82, 84, and 86 are of the fixed volume syringe type and are provided with check valves (not shown) to define the direction of fluid flow. The three syringe pumps 82, 84, and 86 are actuated by a respective DC motor 104, 106, and 108; a separate respective cam (not shown); and linkage 110, 112, and 114, as seen most clearly in FIG. 10. The DC motors are controlled by means of the electronic control mechanism (not shown), which is disposed on a printed circuit board (not shown), located just behind the front plate of the apparatus 10. Encoder wheels 116, 118, and 120 are used to indicate to the electronic control circuitry the physical position of the respective syringe actuating linkage 110, 112, and 114.

Figures 2, 3:
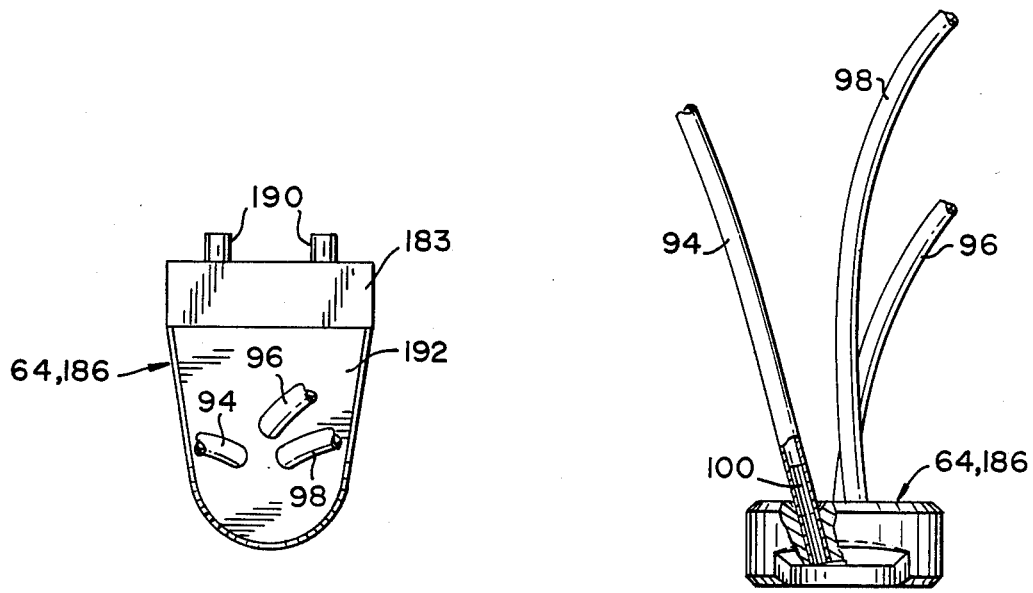
FIG. 2 is a top view of the reagent nozzle dispensing member.
FIG. 3 is a sectional front view of the nozzle member of FIG. 2.

As shown quite clearly in the detail views of FIGS. 3 and 6, for purposes to be explained later herein, the output tube 94 is arranged slightly off center and at an angle of 15° to the vertical, where the tube 94 enters the top of the fluid dispensing member 64 and 186.

Referring to FIGS. 7 and 8, for ease in fabrication and manufacture, the mixing mechanism 50 is seen to comprise a multipart assembly including a central or intermediate, rigid block member 122, a rigid top block member 124, and a rigid bottom, thin, flat planar member 126. The three members 122, 124, and 126 are assembled into a unitary structure and are held together in place by means of four bolts 128 extending through the assembly, as seen in the drawings. The assembled mechanism 50 is vibration damped and insulated from a support bracket 130 by means of individual resilient grommets 132 disposed on each of the four bolts 128. The supporting bracket is attached in a known manner to the inner portion of the apparatus 10.

Figure 13:
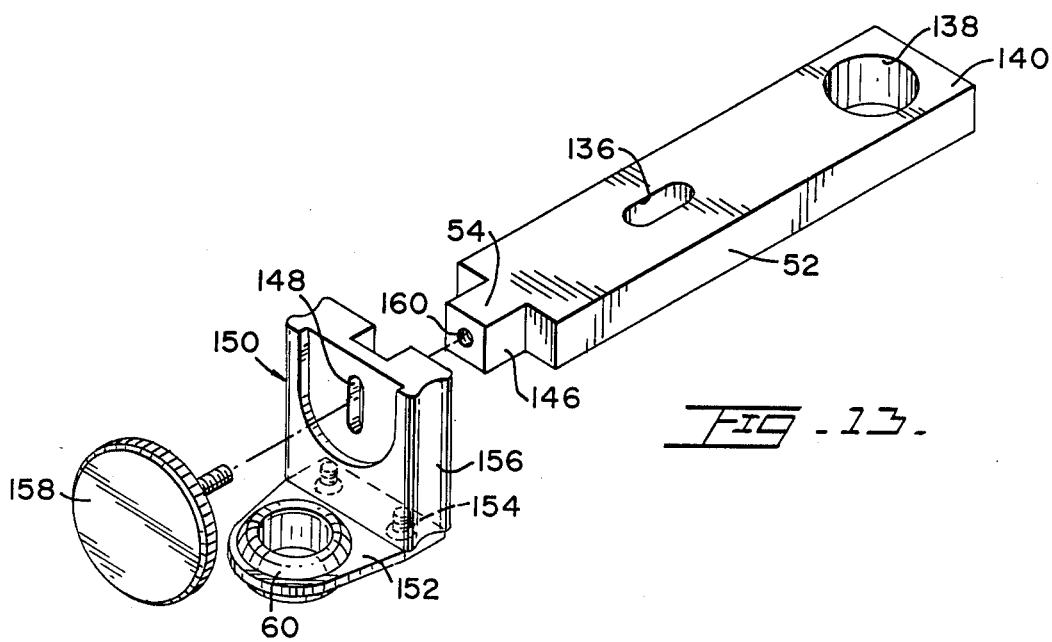
FIG. 13 is a detail view of the adjustment mechanism for the embodiment of FIG. 12.

The central, rigid block member 122 is provided with an enlarged opening 134 for receiving the mixing arm 52. The mixing arm 52 is shown in FIGS. 13 and 14 as an elongated, rigid member having a pivot slot 136 and a circular attachment opening or aperture 138 located at the rear or inboard end 140 thereof. A pivot pin 142 (FIG. 7) is secured to the rigid bottom 126 and extends upwardly through the slot 136 and into a clearance opening 144. As best shown in FIG. 13, the opposite, projecting end 54 of the mixing arm 52 can be modified over that shown in FIG. 11 to provide a forwardly extending securement tang 146, as seen in FIGS. 13 and 14 receivable within an adjustment slot 148 in a rigid, vertically disposed block 150. A flat, planar member 152 is secured to the block 150 by screws 154 and is provided with a grommet 60 for mounting and holding therein the rounded bottom end 62 of the test tube 24. The rigid block 150 is provided with opposite, parallel finger grooves 156 for aid in handling. An enlarged, relatively thin, threaded thumb wheel 158 is receivable in a threaded hole 160 in the tang 146, so as to clamp the rigid block 158 to the arm 52. The test tube 24, when mounted on the grommet 60, is located in front of the thumbwheel 158 for ease in mounting and dismounting the test tube.

Since test tubes, such as those employed in hematology cytometric preparation, are not always uniform in length and thickness, the adjustable lower test tube mounting assembly 156, 158, and 160 of the present invention permits an adjustment up or down; the adjustment to be accomplished while the test tube 24 is seated in place making the adjustment easily accommodated and accurate.

As shown in FIGS. 7 and 8, a DC motor 166, operating at 4,000 rpm, is secured as by bolts 168 to the top block 124 and carries a pinion gear 170. An eccentric shaft 172, including dual bearings 174, is disposed in an opening 176 in the central, rigid block member 122 and carries a driven gear 178. A second bearing 180, on the lower portion of the eccentric shaft 172, is disposed within the opening 138 in the mixing arm 52. A toothed drive belt 182, movable within an opening 184 in member 124, drivingly interconnects the pinion gear 170 and the driven gear 178 for transmitting motion to the eccentric shaft 172. As the eccentric shaft 172 turns, the mixing arm 52 is propelled into elliptical motion by the rotation of the motor 166 and the drive belt 182.

The rotational mixing mechanism 50 can be modified to eliminate the clip 70. As illustrated in FIGS. 4, 5, 6, 12, and 16, a modified reagent liquid dispensing head 186 is formed as two separate portions. A rear portion 188 is secured to the front wall 58 of the apparatus 10 by means of two forwardly projecting pins 190. A front portion 192 is demountably secured to the rear portion 188 by forward ends 194 of the two pins 190. The under side of the forward part of the front portion 192 is shaped to provide an angled ramp 196 at its leading edge 198. The under side of the midsection of the head 186 is provided with a central recess 200 and a short rim or lip 202 at the inboard end of the ramp 196 for loosely supporting the open top 68 of the test tube 24. In use, the bottom 62 of the test tube 24 is seated into the grommet 60, after which the top 68 of the test tube 24 is pushed down the ramp 196 to seat securely behind the short rim or lip 202. To remove the test tube, the operator simple pushes the test tube 24 slightly further down into the resilient grommet 60, after which the test tube 24 can be angled outwardly and removed from the mixing structure.

The electronic control mechanism (not shown) is disposed on a single printed circuit board (also not shown) and provides the timing electronics to control: the automatic or manual reagent delivery, individual priming cycles, continuous mix cycle, short cycle reagent addition, long cycle reagent addition and mixing, and the stop cycle.

To operate the apparatus 10 (FIG. 1) as earlier mentioned, the sample test tube 24 is inserted bottom first into the resilient grommet 60 and then is pressed into the flexible clip 70 or into the modified dispensing head 186 at the top of the tube, which secures the test tube 24 at its top and locates the tube directly below the dispensing member 64. The door 44 then is closed, the appropriate cycle button 26 or 27 is pressed, and the cycle begins.

During operation, the lytic reagent syringe 82 delivers 600 µl per stroke. The stabilizing reagent syringe 84 delivers 265 µl of reagent per stroke. The fixative reagent syringe 86 delivers 100 µl per stroke. The reagents are delivered to the test tube 24 via the flexible output tubing 94, 96, and 98 through the common fluid dispensing member 64 or 186. During either cycle, the syringes deliver one stroke volume of reagents in a timed sequence which is controlled by the timing electronics.

The seven membrane switches earlier described permit the operator automatically or manually to control all the function described above. Each syringe can be primed by depressing its respective priming switch. The operator has two choices for sample preparation. The decision on the cycle chosen depends on the number of samples which are to be prepared and the monoclonal antibodies used. If the operator is preparing a small number of samples, he can use the long cycle which incubates the blood with antibody, by mixing for one minute before lysis. By using this cycle, the operator can prepare one sample, while analyzing another sample on the associated flow cytometer. If the operator, on the other hand, is preparing a large number of samples, then it is simpler to stain the blood in a batch type fashion and use the short cycle to lyse the red cells. This technique is most useful when the sample preparation unit is not in the same room as the flow cytometer, for example, a sample prep room. Once the technician inserts the tube in the unit, and closes the protective door, he will then press the desired cycle button and the unit will initiate the cycle. In the short cycle mode: the sample is mixed for two seconds, the mixer is stopped, lytic reagent is added; the sample is mixed for eight seconds, stopped, stabilizer is added; sample is mixed for ten seconds, stopped, fixative is added; sample is mixed for ten seconds; and the cycle then is terminated. The long cycle is similar to the short cycle with the exception that the sample is mixed for one minute before the lytic reagent is added. The cycle can be stopped at any time during either cycle by depressing the stop switch 14.

The present novel mixing device thus thoroughly mixes, for example, a blood sample, while adding aliquots of reagents from the three different syringes. The initial volume of blood, being 100 ml, can be mixed for 2 seconds or 60 seconds, depending on the choice of the short or long cycle, after which 600 μl of lysing agent is added to the sample tube. The mixture then mixes for eight seconds, at which time the second syringe is actuated, dispensing 265 μl of stabilizing agent. After ten seconds of mixing, the third syringe actuated dispenses 100 μl of fixative into the tube. The total 1,065 ul of mixture then is mixed for an additional ten seconds, after which the tube comes to rest. It should be noted, that by virtue of the structural arrangement of the liquid dispensing member 64 or 186 in relation to the test tube, liquid is dispensed into the tube so that it is swirled around the wall of the tube, and that the eccentric arm design provides for an asymmetric vortex type mixing action, in which the mixing action is optimized for the described process by stopping the mixer driver motor each time a reagent is dispensed into the tube 24.

OPERATION

The mixing sequence is illustrated in FIGS. 15 and 16. With sample material, such as whole blood 204 in the test tube 24, the test tube is placed in the mixing apparatus 10 and the short mixing cycle 35 seconds is selected. The apparatus 10 is started and the test tube 24 is elliptically rotated for two seconds. As seen in FIG. 15, the elliptical rotation of the test tube 24 causes the blood 204 to rise up the wall of the test tube 24 to a particular height 206 (dependent upon the initial volume of fluid in the tube) above the bottom of the test tube above the so-called normal level 208 of that volume of fluid in the tube. It is noted that the blood 204 rises up the test tube in an asymmetric vortex 210, as shown. The blood does not rise from the bottom of the tube up the wall of the test tube to then fall back down the center of the tube, as might be expected in a vortex, but rather the blood rises up along the wall of the test tube 24 and continues to spin along the test tube wall as the elliptical rotation continues. This action results in a planar mixing throughout the area of the vortex. When the rotational motion stops, the fluid blood 204 falls back into the bottom of the test tube 24 and continues to swirl and mix around for a period of time inside the tube.

At the end of two seconds of mixing, the lyse reagent 212 is added to the contents of the test tube 24. The lyse 212 is introduced into the test tube 24 via the dispensing head 64 or 186 at the earlier mentioned angle of 15° to the vertical and off center, as seen in FIG. 16. In this fashion, the lyse 212 strikes the inside wall of the test tube 24 at an angle and swirls 214 downwardly around the wall of the tube before finally reaching any of the fluid in the test tube or the test tube bottom. This prevents splashing the lyse 212 and the blood 204 onto the wall of the test tube 24. The inside wall of the test tube is wetted by this action as the fluid washes down the wall carrying with it any residue material which may happen to be on the wall, thus assuring complete and thorough mixing of the blood 204 and the lyse 212. After an additional eight seconds of mixing, the stabilizing reagent 216 is added vertically from the dispensing head 64 or 186, since the volume and velocity of this reagent isn't sufficient to cause splashing. After ten seconds of mixing with the stabilizing reagent 216, the fixing reagent 218 is added, again from a vertically disposed output tube in the dispensing head 64 or 186. As with the stabilizer 216, the volume and velocity of the fixing reagent 218 is insufficient to cause any appreciable splashing within the test tube 24.

It is noted that, as the test tube 24 is held substantially stationary at its top, there is no danger that the fluids being mixed within the tube can escape out the top of the tube, since the tube velocity at its top is zero.

As seen in FIGS. 14A and 15 the total angular movement of the test tube 24 from left to right relative to the vertical axis is 3.10°, 1.55° from the center of each side, while the total distance moved from left to right is 0.16", 0.08" from the center of each side or 2.03 mm. The total angular movement of the test tube 24 from front to back relative to the vertical axis is 2.32°, 1.16° from center to front and 1.16° from center to back, while the total distance moved from front to back,; is 0.120", 0.06" back and 0.06" front or 1.52 mm. The delivery velocity of the reagents in microliters per second through the constricting tubing 100 of 0.034" diameter or 0.086 cm I.D. is as follows:

a. lyse 212=68.28 cm/sec.
b. stabilizer 216=90.48 cm/sec.
c. fixative 218=34.14 cm/sec.

The present apparatus is essentially accurately repeatable as well as automatic in operation in that each of the two selectable cycle times 35 seconds and 93 seconds are predetermined at the time of manufacture and assembly. By switching the apparatus to the manual mode of operation, the operator, if desired or required, can cycle each reagent syringe pump separately so as to incrementally increase the volume of a selected reagent.

The present novel mixing apparatus is completely accurate as to time and volume thereby producing a consistently repeatable result regardless of the skill of the operator. The mechanism is efficient and foolproof since it is preprogrammed as to desired and required volumes and times.

What we claim is:

1. Sample preparation apparatus in which two or more reagents are dispensed into a mixing container retaining sample material, after which said mixing container is rotated so as to cause the reagents to react with the sample material to prepare it for subsequent use; said apparatus comprising:
   supporting means for supporting said mixing container in a substantially vertical position;
   reagent dispensing means for dispensing said reagents into the top of said mixing container;
   securing means for securing the top of said mixing container relative to said reagent dispensing means; and
   drive means operably associated with said supporting means for providing motion of said supporting means to cause the bottom of said mixing container to move relative to said dispensing means.

2. Apparatus in accordance with claim 1, wherein said supporting means comprises an elongated, rigid member having pivot means intermediate its ends and being free to move at one end, and said rigid member including resilient means for engaging the bottom of said mixing container.

3. Apparatus in accordance with claim 2, wherein said pivot means includes an aperture and a fixed pin engaging said aperture for moving said rigid member about said fixed pin.

4. Apparatus in accordance with claim 3, wherein one end of said rigid member includes an eccentric member engagable with said drive means for rotatably moving said rigid member about said fixed pin.

5. Apparatus in accordance with claim 3, wherein said pivot means and said aperture permits said rigid member to move forwardly and backwardly relative to said pivot means, as well as from side to side, to enable the other end of said rigid member to move in a elliptical motion.

6. Apparatus in accordance with claim 1, wherein the bottom of said mixing container is disposed upon said supporting means and the top of said mixing container is captivated by said securing means, permitting movement relative to said dispensing means, such that the bottom of said mixing container is obliged to partake of a rotary motion, causing the bottom of said mixing container to physically rotate about said dispensing means.

7. Apparatus in accordance with claim 1, wherein said reagent dispensing means includes structure for engaging and demountably retaining the top of said mixing container in contact therewith to align said dispensing means with said top of said mixing container, to avoid any spillage of material from said mixing container while it is being moved.

8. Apparatus in accordance with claim 1, wherein said securing means comprises a pair of resilient members arcuately shaped to partially surround said mixing container, while permitting said mixing container to be introduced and withdrawn from said resilient members.

9. Apparatus in accordance with claim 1, wherein said supporting means supports said mixing container and comprises a compressible member.

10. Apparatus in accordance with claim 9, wherein said compressible member comprises a grommet.

11. Apparatus in accordance with claim 1, wherein said supporting means is adjustable relative to its vertical axis to permit said mixing container to move up and down on said supporting means relative to said reagent dispensing means to accommodate variations in container size.

12. Apparatus in accordance with claim 1, wherein said reagent dispensing means includes multiple input ports, at least one of said ports being angled away from the vertical at approximately 15° relative to said securing means.

13. Apparatus in accordance with claim 1, wherein multiple input ports are disposed on said dispensing means and displaced from one another relative to the axial center of said mixing container, so that removal of said mixing container from said supporting means avoids cross contamination from one input port with another.

14. Apparatus in accordance with claim 12, wherein said reagent dispensing means further includes an outwardly canted or angled ramp terminating inwardly in a ridge or lip and a shallow depression for receiving and seating said mixing container therein in registration and alignment with said ports.

15. Apparatus in accordance with claim 1, wherein said mixing container comprises a cylindrical, elongated, tubular member closed at one end.

16. Apparatus in accordance with claim 1, wherein said securing means secures the top of said mixing container into contact with said reagent dispensing means.

17. A method of sample preparation, in which one or more reagents are dispensed into a mixing container containing sample material, after which the mixing container is moved, to cause the reagents to react with the sample material to prepare the sample material for further use, said method comprising the steps of:
   supporting the bottom of said mixing container with supporting means;
   securing the top of said mixing container into contact with a reagent dispensing means;
   providing asymmetrical vortex mixing drive means operably associated with said supporting means;
   mixing said sample material by rotatively driving said supporting means;
   adding a lytic reagent into said mixing container via said reagent dispensing means and mixing said lytic reagent with said sample material;
   adding a stabilizing reagent to said mixing container and mixing that reagent with said sample material, which by then has been lysed by said lytic reagent, whereby said mixing causes said mixing container to move elliptically relative to said reagent dispensing means, thus assuring complete and gentle mixing of the contents of said mixing container.

18. The method of claim 17, further comprising the step of adding and mixing a fixative reagent with said lysed and stabilized sample material.

19. The method of claim 17, wherein said mixing drive means is operable to move said mixing container at a range of speeds from 900 to 1,800 rpm.

20. The method of claim 18, wherein the steps of adding reagent further comprise mixing said sample material for two seconds; mixing the lytic reagent with sample material for eight seconds; mixing said lysed sample material with said stabilizing reagent for ten seconds; and mixing said lysed and stabilized sample material with said fixitive reagent for ten seconds.

21. The method of claim 17, wherein each of said reagent adding steps is preceeded by first stopping the mixing drive means and then restarting the drive means after the reagent is added, thereby effectively increasing the homogenity of the solution, for producing the desired reagent reactions in a rapid, repeatable fashion.

22. The method of claim 17, in which the step of adding a lytic reagent into said mixing container and asymmetrically vortex mixing said lytic reagent with said sample material is accomplished by dispensing said lytic reagent at a velocity of approximately 70 cm/sec., and the step of adding a stabilizing reagent is accomplished by dispensing said stabilizing reagent at a velocity of approximately 90 cm/sec.

23. The method of claim 18, in which the step of adding and mixing a fixitive reagent with said lysed and stabilized sample material is accomplished by dispensing said fixitive reagent at a velocity of approximately 35 cm/sec.

24. The method of claim 17, wherein the step of mixing said sample material by elliptically driving said supporting means is accomplished by elliptically rotating said sample container between angles of 1.16° and 1.55° relative to said dispensing means.

* * * * *